United States Patent
Oumnia

(10) Patent No.: US 10,966,638 B2
(45) Date of Patent: Apr. 6, 2021

(54) MINIATURIZED ELECTRONIC UNIT FOR INTEGRATION IN ANY SOLE

(71) Applicant: ZHOR TECH, Nancy (FR)

(72) Inventor: Karim Oumnia, Nancy (FR)

(73) Assignee: ZHOR TECH, Nancy (FR)

( * ) Notice: Subject to any disclaimer, the term of this patent is extended or adjusted under 35 U.S.C. 154(b) by 0 days.

(21) Appl. No.: 16/756,397

(22) PCT Filed: Oct. 16, 2018

(86) PCT No.: PCT/FR2018/052578
§ 371 (c)(1),
(2) Date: Apr. 15, 2020

(87) PCT Pub. No.: WO2019/077266
PCT Pub. Date: Apr. 25, 2019

(65) Prior Publication Data
US 2020/0289028 A1   Sep. 17, 2020

(30) Foreign Application Priority Data

Oct. 16, 2017  (FR) ......................................... 1771087
Apr. 26, 2018  (FR) ......................................... 1870497

(51) Int. Cl.
*A61B 5/00*      (2006.01)
*A61B 5/11*      (2006.01)
(Continued)

(52) U.S. Cl.
CPC ............ *A61B 5/112* (2013.01); *A43B 3/0005* (2013.01); *A61B 5/1116* (2013.01); *A61B 5/6807* (2013.01); *H04W 4/80* (2018.02)

(58) Field of Classification Search
CPC ......... A61B 5/11; A61B 5/112; A61B 5/1123; A61B 3/0005; A61B 5/1116; A61B 5/6807; H04W 4/80
See application file for complete search history.

(56) References Cited

U.S. PATENT DOCUMENTS 4,703,445 A   10/1987  Dassler et al.
4,736,312 A   4/1988   Dassler et al.
(Continued)

FOREIGN PATENT DOCUMENTS

EP   1970671 A1   9/2008
EP   2458338 A1   5/2012
(Continued)

OTHER PUBLICATIONS

English translation of International Preliminary Report on Patentability (previously submitted) issued in PCT/FR2018/052578 dated Feb. 17, 2020 (6 pages).

(Continued)

*Primary Examiner* — Max F Hindenburg
(74) *Attorney, Agent, or Firm* — Pearne & Gordon LLP

(57) ABSTRACT

The invention relates to a system of analyzing and quantifying a user's posture and gait, characterized in that it includes a pair 10 of soles 11, 12 each provided with an electronic box 100, 101, 102, each box comprising: an inertial platform, a data processing module 120, 121, 122, a data storage module 130, 131, 132, a means of communication 140, 141, 142, a power source 150.

22 Claims, 4 Drawing Sheets

Figure 1:
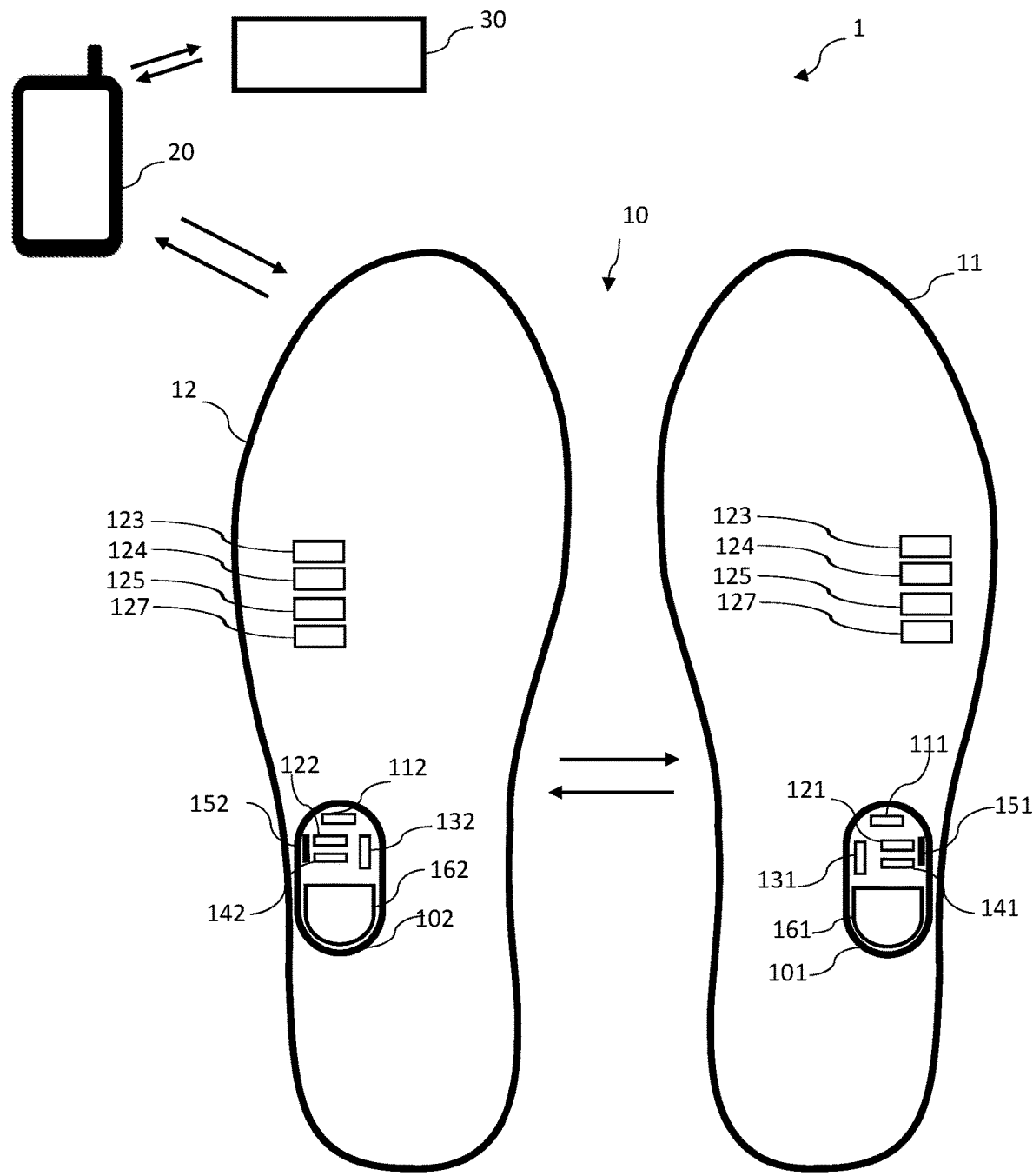

(51) Int. Cl.
*H04W 4/80* (2018.01)
*A43B 3/00* (2006.01)

(56) References Cited

U.S. PATENT DOCUMENTS

| | | | |
|---|---|---|---|
| 9,504,290 B2* | 11/2016 | Andoh | A43B 3/0005 |
| 9,510,776 B2* | 12/2016 | Lee | A61B 5/1116 |
| 2007/0006489 A1 | 1/2007 | Case et al. | |
| 2010/0070316 A1 | 3/2010 | Lieberman et al. | |
| 2015/0351476 A1* | 12/2015 | Lin | B65D 73/00 206/490 |
| 2015/0351665 A1* | 12/2015 | Ross | G01L 5/0052 702/44 |
| 2016/0321947 A1* | 11/2016 | Toronto | A61B 5/1038 |
| 2016/0324445 A1 | 11/2016 | Kim et al. | |
| 2017/0087411 A1 | 3/2017 | Bender et al. | |
| 2017/0105476 A1* | 4/2017 | Morrison | A43B 13/14 |
| 2017/0188950 A1 | 7/2017 | Gazdag et al. | |
| 2017/0241797 A1 | 8/2017 | Kong et al. | |
| 2017/0303827 A1 | 10/2017 | Giedwoyn et al. | |
| 2018/0279915 A1* | 10/2018 | Huang | A61B 5/7264 |

FOREIGN PATENT DOCUMENTS

| | | |
|---|---|---|
| WO | 1998000683 A1 | 1/1998 |
| WO | 2008151642 A1 | 12/2008 |
| WO | 2011157870 A1 | 12/2011 |
| WO | 20140141291 A2 | 9/2014 |

OTHER PUBLICATIONS

International Search Report & Written Opinion issued in PCT/FR2018/052578 dated Jan. 7, 2019 (with translation of ISR), 12 pages.
International Preliminary Report on Patentability (*Rapport Preliminaire International sur la Bevetabilite) issued in PCT/FR2018/052578 dated Feb. 17, 2020 (7 pages)

* cited by examiner

MINIATURIZED ELECTRONIC UNIT FOR INTEGRATION IN ANY SOLE

The invention relates to the field of shoes or more generally to that of footwear. The invention relates more particularly to an electronic box for connected shoe soles.

More precisely, it is a biomechanical data measurement system consisting of two boxes, one arranged in each of the two shoe soles of a same pair, designed to collect and use information on the user's locomotion, walking pattern, posture or balance, or very generally on the user's gait, running or activity.

PRIOR ART

Shoes can be for relaxation, formal, sports, medical, professional or simply recreational use. A shoe consists mainly of, on the one hand, a sole, the lower part which protects the sole of the feet, more or less raised at the back by the heel, and, on the other hand, the upper, the upper part which envelops the foot. It can be limited to the ankle or it can be a high shoe. The sole can be made in two parts. An upper sole layer in direct contact with the user's foot and a lower sole layer in direct contact with the ground or more generally the outside environment. A shoe may also include a removable insole. In this particular case, this sole also consists of at least one upper sole layer and one lower sole layer.

The soles, whether they are insoles or outsoles or the whole shoe, have essentially the original role of protecting the foot from the ground. Their shape varies according to fashion and its vagaries to make room for a multitude of by-products and functions. Nevertheless, for several years now, new information technologies have been accompanying new needs and the world of footwear has been part of this movement. The development of electronics has led to the appearance of so-called connected soles and shoes, which have a wide range of functions.

Among the connected soles or shoes, different systems exist in order to perform a plurality of functions. Some systems are implemented using a single connected shoe or sole. For example, document EP 1970671 and document WO 2011157870 each describe an intelligent shoe designed to allow its user to control different variables (distances traveled, time used, calories consumed . . . ) in order to monitor and improve one's sporting performance. This device, based on a single box, uses an accelerometer only and no gyroscope, and does not detect the walking pattern, nor posture. These systems do not allow to provide a fine analysis of a user's gait, or to generate quality data.

Other systems have been made, implementing sensors positioned on two connected shoes or soles of a same pair. In these systems, the sensors are often dispersed in the shoes or soles, which, on the one hand, impairs user comfort and, on the other hand, leads to significant additional costs associated with the manufacture of the footwear. For example, document US 2017/0241797 describes an apparatus for the user to count steps and distinguish between running and normal walking via a pedometer and an accelerometer. However, this device does not provide information on parameters other than speed. In addition, the apparatus contains only one pedometer and one accelerometer, which does not allow advanced gait parameter values to be generated. In another example, document US 2017/0188950 proposes shoes equipped with pressure sensors and an accelerometer, which can deliver to a smartphone connected via Bluetooth statistics on the wearer's physical activities, such as the number of steps taken or the way the foot is positioned during walking, etc. As for document US 2017/303827, it describes a connected sole device with sensors for studying a person's gait. Equipped with an accelerometer and a gyroscope, this device collects biomechanical data, which is exchanged between the two soles and transmitted to a terminal. However, the various components of this device are scattered throughout the sole, especially the pressure sensors that collect most of the data.

In addition, these devices based on the presence of numerous sensors distributed in the sole (for example pressure sensors) have a shorter service life and often a relatively high thickness that can limit the use of these soles. In addition, calculations are generally not carried out in real time, which results in high data and energy storage requirements.

There are soles using pressure sensors that are supposed to identify posture, but these technical solutions have never so far resulted in a marketable and effective product.

Therefore, there is a need for a new system equipped with two connected shoes or soles allowing to gather sensors sufficient to generate raw quality data in order to finely analyze the gait while being compact, autonomous and resistant.

TECHNICAL PROBLEM

The invention aims to overcome the disadvantages of the prior art. In particular, the invention aims to allow the user to access, especially through the electronic box installed in each of his/her connected soles, information on the exact posture of his/her feet and more generally on his/her gait or activity.

In addition, the invention aims to offer a solution for quantifying the gait which is compact, resistant, highly autonomous and which is preferably configured to carry out a data processing which consumes a minimum of energy.

BRIEF DESCRIPTION OF THE INVENTION

To this end, the invention therefore relates to a system of analyzing and quantifying a user's posture and gait, characterized in that it includes two electronic boxes adapted to be integrated into a pair of soles, a first box being adapted to be integrated into a first sole and a second box being adapted to be integrated into a second sole, each box comprising:
- an inertial platform configured to generate a set of data on the posture, activity or gait of a user of the pair of soles;
- a data processing module configured to pre-process the collected data set according to predefined algorithms and generate information on the posture, activity or gait of a user of the pair of soles;
- a data storage module configured to store the information generated by the processing module;
- a means of communication configured so that an electronic box of at least one of the soles is adapted to transmit the information generated on the user to an external terminal and/or to the other box of the other second sole; and
- a power source.

Such a system allows to reliably track a user's gait. Indeed, the presence of a pair of soles, each including a box protecting an inertial platform, makes it possible to monitor the movement of each of the feet independently. The inertial platform will analyze, in at least three dimensions, the user's posture, movements, locomotion, balance and environment, and more generally everything that is related to the activity of his/her feet or that will be qualified as his/her gait. The inertial platform will not only be able to note the different positions, but also to detect deficiencies or anomalies that appear the users locomotion, pattern, or more generally walking. In addition, since the present electronic box contains all the electronic components required for autonomous operation, such as all the sensors, including calculation modules and a power source, this allows to increase the robustness of the system. This box can advantageously be unique, compact and miniaturized.

Moreover, contrary to the systems proposed in the prior art, the calculation is carried out here at the sole via a data processing module which can correspond to the firmware ("firmware" in Anglo-Saxon terminology) of an electronic board. In this way, the data is processed almost in real time at the electronic box, compared and can then be transferred for visualization on an external terminal. Such a system allows to reduce the load on the memory of the storage module and can therefore increase the autonomy of the system.

According to other optional features of the invention:

the boxes are configured such that raw data generated by the inertial platform of a first box undergoes a first processing step by the data processing module of the first box, and then the processed data is transferred to the second box where it is further processed by the data processing module of the second box. Thus, in particular, the boxes are configured so that a first box receives data from its sole and transmits it to a second box, which processes the received data by comparing it with its own data and generates information on the user's gait or the posture of his/her feet, which information is then transmitted by one of the boxes to the external terminal in real time or in a delayed manner.

the boxes are configured so that the raw data generated by the inertial platform of a first box is transferred to the second box where it is processed by the data processing module of the second box.

the data processing modules contained in the first and second box are configured to compare raw data generated by the inertial platform of the respective box with predetermined patterns and to generate similarity values of the raw data with the predetermined patterns, said predetermined patterns corresponding to a predetermined movement category, one of the processing modules being further configured to select a movement category representative of the raw data generated over a period of time, from the similarity values of the first box and those of the second box. Thus, it is possible to identify a category of movement with a minimum of energy and memory consumption.

each of the boxes contains an electronic board provided with an inertial platform, consisting of at least one accelerometer and at least one gyroscope, and to which can be added other sensors, in particular a magnetometer, a barometer and an altimeter.

each of the boxes, in addition to the electronic board and a power source, can also be connected to a GPS and/or to all types of sensors, in particular physiological sensors, pressure sensors, temperature sensors or any air-conditioning system placed in the sole.

each of the boxes is designed so as to be able to communicate with the second box and/or directly with the external terminal for example through short wave or high frequency signals of the Bluetooth or ANT+ type. This for example in order to exchange its own information on the posture, movement and activity of its foot, from which it received data via its inertial platform and the sensors of its sole. In particular, the first electronic box of the first sole is configured to transmit preliminary user data to the second box of the other sole and said second box is configured to transmit gait information to an external terminal (20).

each electronic box includes at least one support pad, preferably at least two support pads.

each electronic box weighs less than 20 grams.

each electronic box has a thickness less than or equal to 7 mm.

each electronic box has a surface area on its largest side less than or equal to 10 cm$^2$.

each of the electronic boxes includes an outer casing, said outer casing being essentially made of a thermoplastic material, for example a thermoplastic composite material, allowing it to withstand high mechanical stresses, (evaluated and tested under conditions of use—box inserted into a sole or a shoe) corresponding to at least 100,000 impacts of 1000 N at a frequency of 1 Hz or 100,000 impacts of 3000 N at a frequency of 2.6 Hz, said boxes being, furthermore, resistant to dust and humidity at a level of at least IP56.

the system according to the invention allows to associate one or more Android, IOS or other applications with secure data sharing with the user via the external terminal.

the power source of the electronic box can be a rechargeable battery, which can be recharged using different technologies:
  by a charger, with a connector flush with the sole;
  with a mechanical recharging device integrated into the sole, such as a piezoelectric device capable of supplying electrical energy from walking;
  with a non-contact device, for example by induction; or
  with a photovoltaic device.

According to another aspect, the invention relates to a method of quantifying a user's posture and gait, implementable within a system according to the invention. For example implemented within a system including two electronic boxes integrated into a pair of soles, a first box being integrated into a first sole and a second box being integrated into a second sole of a same pair of soles, each box comprising: an inertial platform, a data processing module, a data storage module configured to store the information generated by the processing module, a means of communication and a power source, including a first box integrated into a first sole and a second box integrated into a second sole of a same pair of soles, said method comprising:

A step of generating raw data, by inertial platforms contained in the first and second box, said raw data being generated for a period of time and being a function of a user's gait, A step of pre-processing the raw data, by the data processing modules contained in the first and second box, comprising comparing the generated raw data with predetermined patterns and generating similarity values of the raw data with the predetermined patterns, said predetermined patterns corresponding to a predetermined category of movement, A step of communicating between the first and second box, comprising transmitting, by a communication module, similarity values from the second box to the first box, and A step of selecting, by the first box, a movement category representative of the raw data generated over the period of time, from the similarity values of the first box and those of the second box.

According to other optional features of the method:

it further comprises a step of incrementing a counter associated with the selected movement category and storing the new value of said counter, the pre-processing step includes a sub-step of calculating preliminary values of gait parameters by the first and second box. In particular, the pre-processing step includes a sub-step of calculating preliminary values of gait parameters by the first and second box, said preliminary values of gait parameters being transmitted, by the communication module, from the second box to the first box and the method then includes a step of comparing the preliminary values of gait parameters of the second box with those of the first box so as to generate a consolidated value of gait parameters. In addition, in this case, the method may also include a step of modifying counters associated with the gait parameters and storing the new value of said counters.

it comprises a step of processing the preliminary values of gait parameters of the second box and of the first box so as to select preliminary values of gait parameters to be retained.

it comprises a prior learning step comprising defining a plurality of predetermined gait patterns of a user. These predetermined gait patterns are advantageously associated with movement categories such as walking, climbing stairs, jumping . . . .

Other advantages and features of the invention will appear upon reading the following description given by way of illustrative and non-limiting example, with reference to the appended figures which represent:

FIG. 1, a longitudinal cross-sectional view of the top of two soles, each containing a cavity which will give way to a box, each of the antennas of the boxes being located on the outer edge facing each foot, according to one embodiment of the invention.

Figure 2:
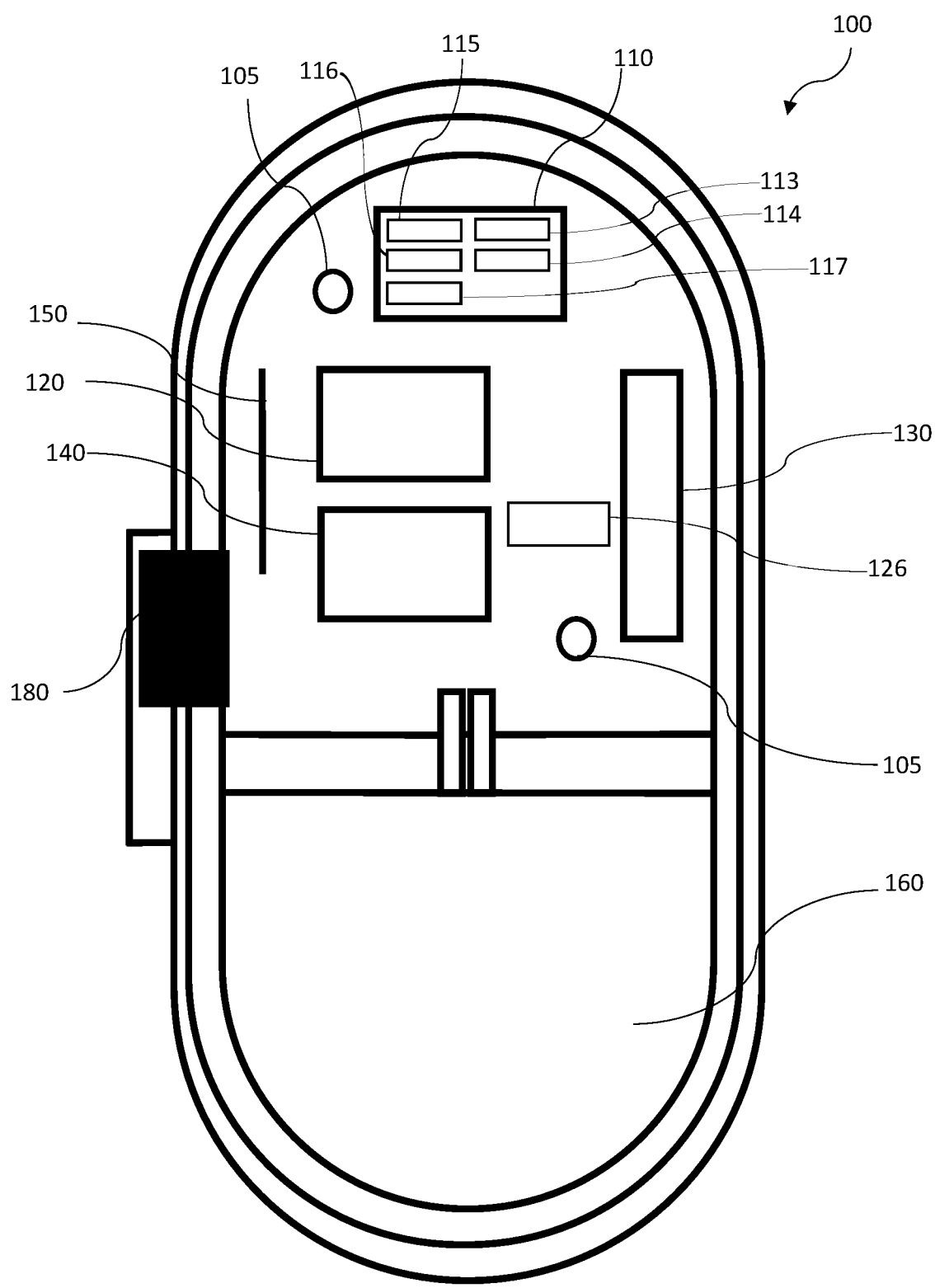

FIG. 2, an open electronic box as seen from above comprising in particular an electronic board, a rechargeable battery, a connector and an antenna.

Figure 3:
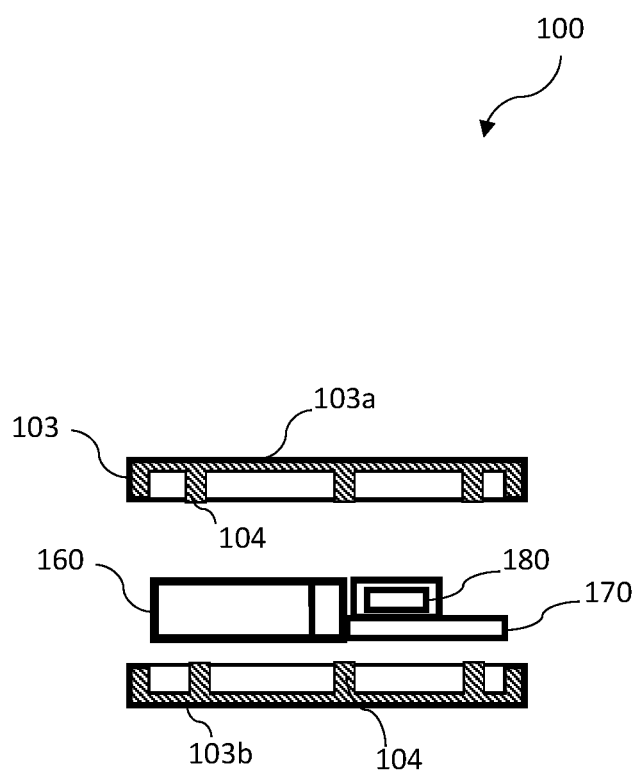

FIG. 3, an electronic box, in exploded and cross-sectional profile view, comprising in particular a rechargeable battery, an electronic board, as well as a two-part outer casing.

Figure 4:
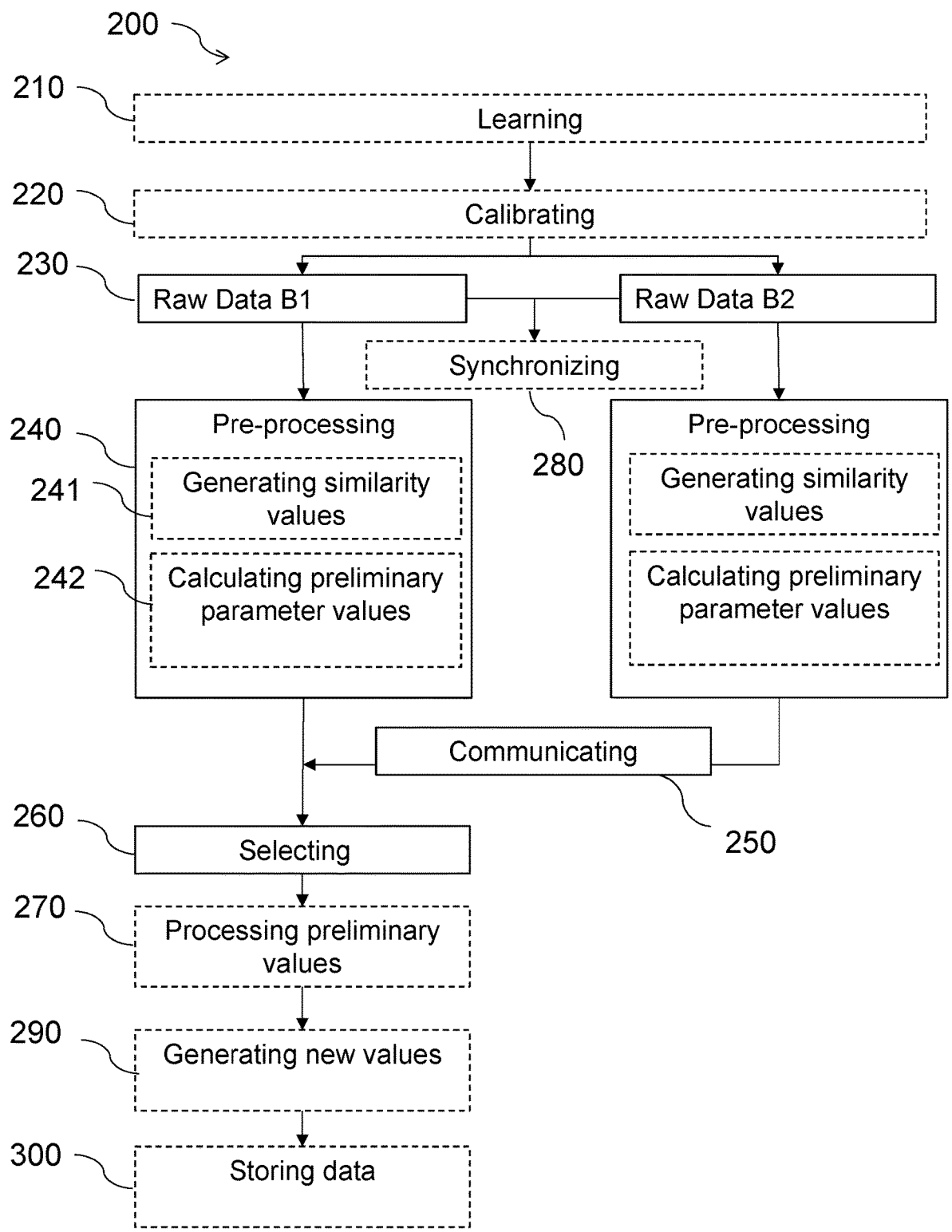

FIG. 4, a representative diagram of the method according to one embodiment of the invention.

Aspects of the present invention shall be described with reference to flow diagrams and/or block diagrams of methods, apparatus (systems) and computer program products according to embodiments of the invention.

In the figures, flow charts and block diagrams illustrate the architecture, functionality and operation of possible implementations of systems, processes and computer program products according to various embodiments of the present invention. In this respect, each block in the flowcharts or block diagrams may represent a system, device, module or code, which comprises one or more executable instructions for implementing the one or more specified logical functions. In some implementations, the functions associated with the blocks may appear in a different order than shown in the figures. For example, two blocks shown in succession may, in fact, be executed substantially simultaneously, or the blocks may sometimes be executed in reverse order, depending on the functionality involved. Each block in the block diagrams and/or flowchart, and combinations of blocks in the block diagrams and/or flowchart, may be implemented by special hardware systems that perform the specified functions or acts or perform combinations of special hardware and computer instructions.

DESCRIPTION OF THE INVENTION

By "sole" is meant an object for separating the users foot from the ground. A shoe may include an upper sole layer in direct contact with the users foot and a lower sole layer in direct contact with the ground or more generally the outside environment. A shoe may also include a removable insole.

In the following description, "gait", within the meaning of the invention, corresponds to the user's posture, movements, locomotion, and balance. The balance corresponds in particular to the postural balance linked to the stability of the body and more particularly to the stability of the users center of gravity. Nevertheless, it can integrate static and dynamic balance as well.

The "gait quantification" corresponds, within the meaning of the invention, to the assignment of one or more values, for example a score, a ranking or a mark to a trajectory or a movement of a users foot. This gait quantification allows to obtain one or more biomechanical parameter values representative of the gait and can be performed based on many different linear or non-linear size scales (for example 1, 5, 10, 100).

By "biomechanical parameter" and more particularly by "parameter calculated from movement data" is meant, within the meaning of the invention, the result of a transformation of the measured trajectory of a users foot into one or more values.

By "model" or "rule" or "algorithm" is to be understood, within the meaning of the invention, a finite sequence of operations or instructions for calculating a value through a classification or partitioning of the data within predefined groups Y and for assigning a score or ranking one or more data within a classification. The implementation of this finite sequence of operations allows, for example, to assign a label Y to an observation described by a set of characteristics or parameters X, using for example the implementation of a function f likely to reproduce Y, having observed X.

$$Y=f(X)+e$$

where e symbolizes noise or measurement error.

By "pattern" is meant the way in which the user unrolls his/her foot when walking or running.

By "process", "calculate", "determine", "display", "transform", "extract", "compare" or more broadly "executable operation" is meant, within the meaning of the invention, an action performed by a device or processor unless the context indicates otherwise. In this respect, operations refer to actions and/or processes of a data processing system, for example a computer system or electronic computing device, which manipulates and transforms the data represented as physical (electronic) quantities in the memories of the computer system or other devices for storing, transmitting or displaying information. These operations can be based on applications or software.

The terms "application", "software", "program code", and "executable code" mean any expression, code or notation in a set of instructions designed to cause data processing in order to perform a particular function directly or indirectly (for example after an operation of converting into another code). Examples of program code may include, but are not limited to, a subprogram, function, executable application, source code, object code, library and/or any other sequence of instructions designed for execution on a computer system.

By "plastic composite" is meant, within the meaning of the invention, a multi-component material comprising at least two immiscible components in which at least one component is a polymer (thermoplastic or thermosetting) and the other component may be a reinforcement such as a fibrous reinforcement.

By "fibrous reinforcement" or "fibrous substrate" is meant, within the meaning of the invention, several unidirectional rovings or a continuous filament mat, fabrics, felts or non wovens, which may be in the form of strips, webs, braids, wicks or pieces.

By "polymer" is meant either a copolymer or a homopolymer. By "copolymer" is meant a polymer involving several different monomer units and by "homopolymer" is meant a polymer involving identical monomer units.

By "thermoplastic polymer" is meant, within the meaning of the invention, a polymer which is generally solid at room temperature, may be crystalline, semi-crystalline or amorphous, and which softens during a temperature increase, in particular after passing through its glass transition temperature (Tg), and flows at higher temperatures. Examples of thermoplastics are, for example: low-density polyethylene (HDPE), polyethylene terephthalate (PET) or polyvinyl chloride (PVC).

By "thermosetting polymer" is meant a plastic material that is irreversibly transformed by polymerization into an insoluble polymer network.

By "removable" is meant the ability to be detached, removed or disassembled easily without having to destroy the means of attachment, either because there is no means of attachment, or because the means of attachment can be easily and quickly disassembled (for example notch, screw, tongue, lug, clips). For example, by removable is to be understood that the object is not fixed by welding or other means not intended to allow the object to be detached.

In this description and even before, the same references are used to refer to the same elements.

Existing devices or systems usually have a plurality of sensors (for example pressure sensors) distributed throughout the shoe and/or sole. Such a distribution of sensors leads to a reduction in the robustness of the system. In addition, these devices or systems are usually intended to produce raw data that is then analyzed at an external terminal. Faced with these shortcomings, the inventor developed a system 1 for quantifying a user's gait as schematized in FIG. 1.

As a reminder, both feet contain a quarter of all the bones in the human body. In each foot, 26 bones, 33 muscles, 16 joints and 107 ligaments can be identified. The feet bear the weight of the body in the standing position and allow locomotion, playing a key role in balance, damping and propulsion. Feet also perform several types of movements. In addition, the feet have almost 7200 nerve endings, so that all diseases and other disorders, especially neurological ones, can be detected directly or indirectly in our feet and, on the other hand, can be detected from the way we walk or move.

In order to pursue this objective, the invention consists of an autonomous technology inserted in a compact and miniaturized box of a few grams, which is inserted in each of the two insoles and/or outsoles of shoes of a same pair.

The choices described hereafter allowed the inventors to obtain a compact and miniaturized box of a few grams that is nevertheless able to withstand repeated pressures and forces when walking, running, jumping or during other sports activities.

According to a first aspect, the invention relates to a device integrated into an electronic box inserted in each of the two insoles and/or outsoles of shoes of a same pair and collecting in particular data on the user's locomotion, pattern or balance, or very generally the user's walking or activity, which it communicates to the box of the other sole and to an external terminal, in particular through short wave or high frequency signals of the Bluetooth type, for the purpose of analyzing and determining the posture/movement/activity of each of the feet, said box comprising in particular an electronic board of the PCBA type and a power source, characterized in that this box, which has an internal data storage memory, processes and exchanges its data according to predefined algorithms, before transmitting it to the external terminal for processing by a dedicated application.

The invention also relates to a system for collecting and using information on the user's locomotion, pattern or balance, or very generally the user's walking or activity, characterized in that it comprises an electronic box inserted in each of the two insoles and/or outsoles of shoes of a same pair and collecting data which it communicates to the box of the other sole and to an external terminal, in particular through short wave or high frequency signals of the Bluetooth type, for the purpose of analyzing and determining the posture/movement/activity of each of the feet, said box comprising in particular an electronic board of the PCBA type and a power source, characterized in that this box, which has an internal data storage memory, processes and exchanges its data according to predefined algorithms, before transmitting it to the external terminal for processing by a dedicated application.

In particular, the invention relates to a system including two boxes as described below. In particular, it relates to a system including two electronic boxes 100, 101, 102 which can be integrated into a pair 10 of soles, a first box being adapted to be integrated into a first sole and a second box being adapted to be integrated into a second sole.

In particular, the system 1 according to the invention may include a pair 10 of soles including the electronic boxes 100, 101, 102 according to the invention and possibly an external terminal 20.

The soles 11, 12 usable within the context of the system 1 according to the invention may, for example, correspond to outsoles or insoles of shoes. These soles can be removable or permanently integrated into the bottom assembly of the shoes.

Classically, the soles 11, 12 composing said pair 10 of soles, each include an electronic box 100, 101, 102. As shown in FIG. 1, the electronic box 101, 102 is preferably positioned at a midsole portion.

An electronic box 100 according to the invention is detailed in FIG. 2. Weighing only a few grams and being small in size, this electronic box 100 fits into any insole and/or outsole in a space-saving manner. This low volume limits the impact on user comfort and has the advantage of optimizing production costs by making it cheaper and simpler to integrate this technology into the sole during the industrial process.

The choice of the material of this electronic box is made in order to ensure its solidity as well as the possibility of inserting it in a sole. Indeed, it should be possible to manufacture a product that can, on the one hand, withstand the weight of a person and, on the other hand, be easily inserted into a sole or shoe. Combining miniaturization and resistance of the box is a real challenge: many prototypes had to be made before determining the material that would allow such a box to be inserted into a sole without altering the comfort thereof.

Advantageously, each electronic box 100 includes an outer casing 103, said outer casing consisting essentially of a material of the plastic composite type selected from: a thermoplastic composite material or a thermosetting composite material. Preferably, the material used is based on a thermoplastic such as polycarbonate and may include nylon or fiberglass. Indeed, polycarbonate has the advantage of being thermoformable, mechanically resistant and flame retardant, which is advantageous during the ultrasonic welding process detailed below.

The choice of a polymer material, for example a plastic composite polymer material, allows to combine lightness, efficient signal transmission and above all strength. Advantageously, the casing is rounded, namely it does not have an angle of less than 95°. This casing shape allows to improve user comfort.

Thus, each electronic box is preferably light and weighs for example less than 20 grams, less than 10 grams, preferably less than 8 grams and more preferably less than 6 grams. In addition, it may have a thickness of less than 7 mm, or less than 5 mm, preferably less than 4 mm and more preferably less than 3 mm. This allows it to be easily integrated into a shoe/sole without altering user comfort in the shoe. Finally, each electronic box has, for example, less than 10 $cm^2$ of surface area on its largest side, preferably less than 5 $cm^2$ of surface area on its largest side, more preferably less than 4 $cm^2$ and even more preferably less than 3 $cm^2$.

Preferably, the outer casing 103 of the electronic box 100 has an upper part 103a and a lower part 103b which are welded. Such a weld, for example an ultrasonic weld, increases the water resistance of the electronic box. Alternatively, the upper part 103a and the lower part 103b can be separated by a polymer seal and held together by removable fastening means. Thus, each electronic box can include an outer casing formed in two parts and a seal positioned between two parts of the outer casing.

Preferably with a rounded shape to increase its mechanical resistance, it must be assembled in such a way as to maintain a perfect seal and make the interior containing the electronic board and the power source protected from humidity and dust.

Each electronic box advantageously integrates support pillars or pads 104 in order to reinforce its solidity, preferably one pad/$cm^2$ to withstand the pressures and impact forces of the movements of the foot. Inserting such pads allows the box to better withstand the weight of a person. Advantageously, these pads or this low wall, also allow to fix an electronic board in order to fix the center of inertia so as not to distort the measurements. Thus, preferably, the electronic box 100 according to the invention includes at least two support pads 104, more preferably at least three support pads 104 and even more preferably at least four support pads 104.

In addition, the electronic box 100 according to the invention may include a polymer low wall positioned between the power source and the electronic board so as to increase its robustness. Such a low wall has, for example, a height corresponding to the height of the box, a thickness between 0.5 and 3 mm and a length between ⅗ and 5/5 of the width of the power source.

Advantageously, the electronic box 100 includes an electronic board with at least one opening 105 allowing the passage of at least one support pad 104, preferably at least two openings 105.

In addition, in order to further increase the robustness of the system, each electronic box includes a shock-absorbing material such as polymer foam (for example polyurethane, polyether). According to one embodiment, the shock-absorbing material has a density between 20 kg/$m^3$ and 50 kg/$m^3$. Such a protective foam layer also allows to insulate the board from vibrations and humidity.

Preferably, each of the boxes (for example right and left) has a shape different from the other box. For example, it has a protrusion that is not present in the same shape on the other box. Such a physical characteristic allows to differentiate the two boxes, right or left, when they are integrated into a shoe or sole without inverting the center of inertia.

According to one embodiment of the invention, the electronic board is inserted in a compartment of the box specially designed to receive it.

According to another embodiment, the electronic box 100 is formed by the encapsulation of its components. For example, the encapsulation can take the form of an encapsulating coating or a resin (for example silicone, epoxy, polyurethane). The encapsulation of all components (for example inertial platform, processing module . . . ) offers good insulation and thus combines good electrical properties with excellent mechanical protection.

In addition, the electronic box according to the invention includes an inertial platform 110, 111, 112 configured to generate a set of data on the gait of a user of the pair 10 of soles.

During a users walk, the inertial platform 110 acquires signals representative of a movement parameter (acceleration and/or speed, for example angular velocity) of the foot along the X, Y, Z axes. In addition, this data can then be processed to generate at least one acceleration signal. The inertial platform consists for example of at least one accelerometer 113 and one gyroscope 114. Preferably, it includes several accelerometers and gyroscopes.

The electronic box may also include one or more magnetometers 115 in order to acquire three additional raw signals corresponding to the values of magnetic fields in three dimensions.

In addition, each electronic box can include an inclinometer, a barometer 116, a temperature sensor 126 and an altimeter 117 for increased accuracy. An electronic box can also be connected to an air-conditioning system 127 and/or other sensors, including a GPS 123, a physiological sensor 124, and a pressure sensor 125.

In addition, the electronic box according to the invention includes a data processing module 120, 121, 122 configured to transform the data set generated using predefined algorithms. Indeed, the device or system according to the invention allows the data received via the sensors located in the insoles and/or outsoles to be processed according to one or more algorithms in each of the boxes, said boxes being configured as a Slave box, which receives the data from its sole/shoe and transmits it to the Master box, said Master box (main box) which receives data from the Slave box, processes it by comparing it with its own data and generates information on the users posture in general and his/her feet in particular, information which the box transmits to the terminal in real time or in a delayed manner.

The processing module 120, 121, 122 allows 3D analysis of the users posture, movements, locomotion, balance and environment, and more generally everything that will be qualified as his/her walking, based on the data collected by the inertial platform and any additional sensors placed in the sole.

This processing module can be used to generate biomechanical gait parameters. Advantageously, the data processing module 120 is capable of transforming the data set into at least one biomechanical gait parameter, said biomechanical gait parameter preferably being selected from: posture, pronation, supination, impact force, impact zone, step length, contact time, flight time, limping, propulsion force, balance and several other parameters relating to the user and describing his/her gait, postures and movements.

In addition, processing by the data processing module may advantageously comprise segmenting the data into a plurality of phases. Preferably, the data processing module is capable of segmenting a step into at least four phases such as: the impact phase (corresponds to the precise moment the foot contacts the ground), the support phase (takes place from the impact phase until the heel is detached from the ground), the propulsion phase (begins when the heel has left the ground and ends when the first toe has left the ground) and the flight phase (begins when the first toe has left the ground and ends when the heel touches the ground).

More particularly, the cutting or segmentation of the step can help identify the main support areas of the user Thus, the system can be used to measure the shape of the step during walking or any other activity of the user in order to determine possible malformations of the user's feet and postures.

The information generated will then be transmitted to the second box by a transmission of signals which can be of the Bluetooth type.

When an electronic box is not able to communicate in real time with the other box and/or with the terminal, it stores the collected information and will transmit it in delayed mode when the exchange is possible again. This delayed transmission of the collected data is made possible using the storage capacity each of the electronic boxes is provided with.

Thus, the electronic box according to the invention includes a data storage module 130, 131, 132, configured to store at least part of the transformed data and/or data generated by the processing module. As already discussed, the device or system according to the invention is such that it allows operation with a low-capacity data storage module. For example, the data storage module 130, 131, 132 may advantageously have a memory capacity of less than 512 KB, preferably less than 128 KB, more preferably less than 32 KB and even more preferably less than 16 KB. In particular, the storage module can correspond to available memory on a CPU.

In addition, the electronic box according to the invention includes means of communication. Thus, in particular, each of the boxes, whether Slave or Master, is designed to be able to communicate independently with the other one and/or directly with the terminal in order to be able to exchange its own information on the posture/movement/activity of its foot, the data of which it has received via the various sensors of its insole and/or outsole of the shoe.

Preferably, the electronic box according to the invention includes a first means of communication 140, 141, 142 configured so that the electronic box 100 of at least one of the soles is capable of transmitting at least part of the transformed data to an external terminal 20. This data can be transmitted in real time or in delayed mode to an external terminal 20. The external terminal 20 can for example be a remote system such as a tablet, a mobile phone ("smartphone" in Anglo-Saxon terminology), a computer or a server.

Advantageously, each electronic box further includes a second means of communication configured so that the electronic box 101 of a first sole is able to communicate with the electronic box 102 of a second sole, and in that at least one data processing module 121, 122 is configured to calculate, preferably jointly, sets of data generated from the two soles 11,12, and more particularly from the inertial platform, composing the pair 10 of soles. Indeed, the calculation of certain biomechanical parameters of interest requires the data from both soles.

The first and second means of communication may consist of one and the same means.

The first and second means of communication are capable of receiving and transmitting the data over at least one communication network. Preferably the communication is operated via a wireless protocol such as wifi, 3G, 4G, and/or Bluetooth. Preferably, the communication protocol is a BLE or ANT+ protocol. These communication protocols allow for low power consumption.

Advantageously, because of its confinement inside a box placed under the body of a person, the antenna 150, 151, 152 should preferably be placed inside the box on the side facing the outside of the sole. This positioning of the antenna is preferable since laboratory tests have shown that 70% of the signal emitted from a sole or shoe is absorbed by the human body. This antenna must therefore be positioned on the periphery of the foot and oriented in such a way that the signal can always be transmitted to the external terminal and/or the box of the second sole. Preferably, the antenna can be an antenna printed on an electronic board. Alternatively, the antenna can be printed on an inner side of the box and connected to the electronic board by wiring. The antenna 150, 151, 152 can preferably be positioned on a lower part in relation to the electronic board. Thus, the electronic board makes contact with the antenna.

In addition, the electronic box according to the invention includes a power source 160, 161, 162. The power source is preferably a battery, rechargeable or not. Preferably the power source is a rechargeable battery. In addition, it can be combined with a system for recharging by movement or with external energy. In particular, the system for recharging with external energy can be a wired recharging system, an induction recharging system or a photovoltaic system.

In addition, the electronic box according to the invention may include a wired connection means, preferably protected by a removable tab. This wired connection can be for example a USB or FireWire port 180. Advantageously, the USB port 180 is also resistant to water or humidity. In addition, the USB port 180 is advantageously surmounted by a polymer beam to give it greater strength in use. This wired connection means can be used as mentioned above to recharge the battery but also to exchange data and for example to update the firmware of the electronic board carrying the various components of the electronic box.

Preferably, the removable tab or USB cover allows to protect the USB port from foreign objects. For example, the removable tab can be used to protect the USB port from water or dust. Such a tab can preferably be made of an elastomer or polyurethane type polymer.

These various components of the electronic box are preferably arranged on an electronic board 170 (or printed circuit). In addition, the various means and modules of the electronic box 100 are represented separately in FIGS. 1 and 2, but the invention may provide for various types of arrangement such as, for example, a single module combining all the functions described here. Similarly, these means can be divided into several electronic boards or gathered on a single electronic board.

In addition, the system 1 has an external terminal 20 capable of receiving data. The external terminal 20 is usually a tablet, a mobile phone ("smartphone" in Anglo-Saxon terminology), a gateway, a router, a computer or a server. It may be able to transfer this data to a remote server 30. It is then possible, for example, to access this remote server via a web interface.

Advantageously, a dedicated application is installed on this external terminal in order to process the information transmitted by the boxes and allow the user to interact with the invention.

Advantageously, according to one embodiment of the invention, the two boxes will preferably be set up as a Main box and a Secondary box. The Main box will receive data on the position and/or activity in which the Secondary sole is; the Main box will process this data and extract information from it in all circumstances (for example, when the user is in a kneeling position, soles raised in a more or less vertical manner, each of the boxes will note that its sole is in a raised position more or less perpendicular to the ground; the Main box noting that it is in the same position as the Secondary box, it will be able to deduce that the user is in a kneeling position).

Therefore, even if the two soles are in different positions, the two boxes continue to detect the positions of each sole in order to record changes in the users posture. This continuous detection of the users postures allows, by comparing over time, to accurately record changes in the users walking, posture or physical, sporting or professional activity, so that the device can also detect any possible anomalies, such as a possible limp.

The box will not only be able to note the different positions, but also to detect deficiencies or anomalies that appear in the locomotion, balance, or more generally in the users walking.

The Main Box will analyze and store the collected data and then transmit the information in real time or in a delayed manner to the terminal. Using the storage module of each of the boxes, most of the data collected can be stored as long as the boxes are not connected to an external terminal, so that there is no loss of data or information about the user.

According to one embodiment of the invention, the Secondary box can also transmit the collected data to an external terminal.

In addition to analyzing the gait and activity of its user, this invention aims to identify deficiencies or problems related to the posture of the feet. This posture is indicative of the users mechanical, physical or physiological problems, especially when walking.

From the posture of the foot and its movement, all kinds of information are measured by the electronic board located in the box. The user may have an improper gait, irregular steps, inadequate walking pattern, undetected pronation or supination . . . .

This box will be able to analyze the data relative to the postures of each of the two feet, detecting several anomalies, perceptible by the simple analysis of the user's locomotion, pattern or balance, or very generally the users walking or activity.

According to another aspect, the invention relates to a method 200 of quantifying a user's gait, preferably implemented within a system according to the invention.

The inventors have tested several methods in order to quantify a users posture and gait without altering his/her comfort and while minimizing the energy consumption of the method. Most of the methods tested have a too high energy consumption, which results in a high energy requirement and therefore larger components, which affects user comfort. Indeed, the inventors have, during tests of the usual inertial platform data processing methods, highlighted an excessive consumption of the energy stored in the box as well as of the memory. Indeed, with conventional processing methods, such as those using sliding window pattern analysis from raw data from both feet, power and memory consumption reduced the device's autonomy to a few tens of minutes. This was the case even when the calculations were carried out on telephones, connected watches or remote servers.

The inventors have therefore developed a new method of quantifying a users posture and gait that can be implemented at the boxes integrated into soles. In particular, this method can give relevant results on the gait despite a reduced memory size (for example between 128 KB and 512 KB) whereas previous methods would have required much more memory or much larger power sources.

To this end, the inventors have developed a method 200 of quantifying a user's gait (namely posture and gait) which can be implemented by one of the systems of the invention and is particularly suitable for implementation within a system of quantifying a user's posture and gait including a first box 101 integrated into a first sole and a second box 102 integrated into a second sole of a same pair of soles, the method comprising:

A step of generating 230 raw data, by inertial platforms contained in the first and second box, said raw data being generated for a period of time and being a function of a users gait, A step of pre-processing 240 the raw data, by the data processing modules contained in the first and second box, comprising comparing the raw data with predetermined patterns and generating similarity values of the raw data with the predetermined patterns, A step of communicating 250 between the first and second box, comprising transmitting, by a communication module, similarity values (raw data with the predetermined patterns) from the second box to the first box, A step of selecting 260, by the first box, a predetermined pattern representative of the raw data from the similarity values (raw data with predetermined patterns) of the first box and those of the second box, A step of storing 300 the new advanced gait parameter value by the first box, The method according to the invention comprises a prior learning step 210, comprising defining a plurality of predetermined gait patterns of a user. Thus, the repetition of a users movements, postures and gait over a given period of time is recorded and classified according to a plurality of patterns, for example of the static or dynamic type. Thus a certain dynamic pattern represents a user's movement such as a "step" and a static pattern represents a user's "kneeling" type posture. In particular, the predetermined patterns may have been normalized to a time period corresponding to an event, for example, the event may be a step. In this case, the step can be identified by classical methods of studying the movement of the step such as the Pan-Tompkins method or the detection of maxima. This in order to obtain patterns that are representative of a user and may vary according to the user or the field of application.

The method according to the invention also comprises a prior step of calibrating 220 by a calibration module, between a first and second box comprising the emission of a signal by the first box and the reception of the emitted signal by the second box in order to calibrate a time measuring means, preferably a clock. Such a calibration allows the first and second box to detect and collect a users posture or gait data on a same time window. Indeed, the data collected by the first and second box is analyzed two by two. Thus, the collected data will be analyzed in parallel, which avoids any discrepancy between the data and any analysis errors. Preferably, calibration between the two boxes is performed instantly and in real time.

Advantageously, if one of the boxes were to disconnect or lose time synchronization with respect to the other box, the method comprises a step of synchronizing 280 the boxes. Thus, a search signal is sent by the connected box, the disconnected box receives the search signal and synchronizes to the connected box. In addition, following synchronization, the data collected by the disconnected box is recovered.

The method according to the invention has a step of generating 230 raw data, by inertial platforms contained in the first and second box, said raw data being generated for a period of time and being a function of a users gait. The raw data is related to a users posture, activity or gait. The inertial platform of the first and second box generate the raw data via different sensors contained in the boxes. The raw data can thus be taken from the gyroscope or the accelerometer contained in each box. In addition, according to an advantageous embodiment, the raw data is collected by the two boxes over a predetermined period of time that can range from milliseconds to seconds. Preferably, the generated raw data overwrites previously generated raw data. Thus, the raw data is not saved in the long term, that is to say for a period of time of more than 30 seconds, preferably more than 15 seconds, more preferably 5 seconds. This allows both a reduction in energy consumption and the use of compact components, resulting in greater user comfort.

The method according to the invention comprises a step of pre-processing 240 the raw data, by the data processing modules contained in the first and second box, comprising comparing the raw data with predetermined patterns and generating 241 similarity values of the raw data with the predetermined patterns. Advantageously, the pre-processing step comprises comparing by the first and second box the generated raw data with respect to the plurality of predetermined patterns and generating similarity values of the raw data with the predetermined patterns. The pre-processing comprises testing the whole plurality of patterns on each set of raw data generated on both the first box and the second box. Thus, using this pre-processing it is possible to categorize the raw data according to predetermined categories. There are different types of categories such as stepping, walking up a step, walking down a step, striding, jumping, flight time, walking on flat, being static, trampling, kneeling . . . . The number of categories and the type of category depend on the application or destination of use. The raw data generated is then compared to the predetermined patterns. Thus, it is possible to modify, add, delete the different types of categories. The whole plurality of patterns are tested at the same time on the raw data. In particular, over a given period of time, the raw data is pre-processed in order to determine a plurality of dots which is compared to each pattern of the plurality of patterns, which allows to generate a similarity value for each of the patterns. This allows to reduce the memory space used, the time for pre-processing the raw data and thus to minimize power consumption. In fact, the absence of repetitive pre-processing, loading at different times on each piece of data of the different patterns allows to reduce the consumption of memory space, energy and machine time. This also allows the use of compact components offering greater comfort.

Once the raw data is pre-processed and compared to the predetermined patterns, similarity values are generated. A similarity value is generated for the association of each piece of raw data to each type of predetermined patterns. The similarity value is calculated by the inertial platform of the first and second box. Advantageously, since the data is synchronized, a similarity value is calculated for a same period of time and for each of the patterns twice, once by the first box and a second time by the second box. It is thus possible to quantify a users posture or gait more reliably and with improved accuracy.

Preferably, the pre-processing step can include a sub-step of calculating 242 preliminary values of gait parameters by the first and second box. With this calculation step comprising in particular the implementation of a plurality of calculation functions, or calculation rules, so as to generate a plurality of preliminary values from the raw data collected, by the first or second box. These gait parameters may, for example, be related to stride length, flight time, impact force, foot position during the ascending or descending phase, or any other parameter related to a user's gait, activity or posture, such as pronation or supination. In particular, these preliminary values of gait parameters are calculated for each set of raw data generated over a period of time and by each box. These preliminary values of gait parameters allow for more precision and a better understanding of a users gait, activity or posture.

The method according to the invention further comprises a step of communicating 250 between the first and second box, comprising transmitting, by a communication module, similarity values of the raw data with the predetermined patterns from the second box to the first box. This step of communicating between the first and second box can be carried out according to a predefined time frequency, for example the transmission can be carried out every second, or every two seconds, or for any other predefined time frequency. This step allows to gather all the data and especially similarity values on a single box, preferably on the first box. As a reminder, preferably each predetermined pattern is therefore associated with two similarity values, one from the pre-processing of the raw data of the first box and the other from the raw data of the second box. In addition, this communication step may include transmitting preliminary values of gait parameters from a second box to a first box, or vice versa.

The method comprises a step of selecting 206, by the first box, a movement category representative of the raw data from the similarity values of the first box and those of the second box. Thus, the similarity values allow the first unit to assign to the raw data generated by the two boxes a movement category, for example from a list of predetermined movement categories. In particular, this step comprises selecting a movement category if the second box has transmitted to the first box a corresponding predetermined pattern with a generated similarity value greater than a predetermined reliability percentage and stored for each predetermined pattern. This allows only reliable predetermined patterns to be taken into account before quantifying a users posture and gait.

The method also comprises a step of processing 270 the preliminary values of the gait parameters of the second box and the first box in order to select preliminary values of gait parameters to be retained. In addition, this step may be followed by a step of generating 290 a new gait parameter value by the first box as a function of a selected representative movement category, preliminary values of selected gait parameters, a previously stored gait parameter value and possibly a predetermined threshold. The previously stored gait parameter value is defined for each gait parameter. Thus, it is possible to quantify a users gait and posture reliably and accurately, while ensuring low energy consumption and optimal comfort.

In addition, the method according to the invention also includes a step of comparing the preliminary values of gait parameters of the second box so as to generate a consolidated value of gait parameters for the period of time. Preferably, the method may also include a step of transmitting the new advanced gait parameter value of the stored data to an external terminal. This transmission is preferably made on an ad hoc basis. The transmission frequency can therefore be greater than 100 ms, preferably greater than 1 second. For example, the transmission is every 10 seconds. The external terminal can correspond to a user terminal and include a computer, a digital tablet, a mobile phone, or more generally any device for a user to communicate with the terminal.

The method comprises a step of storing 300 the new advanced gait parameter value by the first box. Thus, in contrast to the raw and/or pre-processed data that is saved for a short time, for example on a cache, the new advanced gait parameter value is stored for a longer time, for example on a memory.

The invention claimed is:

1. A system of analyzing and quantifying a user's posture and gait, said system including two electronic boxes configured to be integrated into a pair of soles, a first box being configured to be integrated into a first sole and a second box being configured to be integrated into a second sole, each said box comprising:
   an inertial platform configured to generate a set of data on the posture, activity or gait of a user of the pair of soles;
   a data processing module configured to pre-process the collected data set according to predefined algorithms and generate information on the posture, activity or gait of a user of the pair of soles;
   a data storage module configured to store the information generated by the processing module;
   a means of communication configured so that the electronic box of at least one of the soles is configured to transmit the information generated on the user to an external terminal and/or to the other box of the other sole; and
   a power source;
   wherein the boxes are configured such that the raw data generated by the inertial platform of the first box undergoes a first processing step by the data processing module of the first box, and then the processed data is transferred to the second box where it is further processed by the data processing module of the second box.

2. The system according to claim 1, wherein the data processing modules contained in the first and second boxes are configured to implement a step of preprocessing of the raw data, comprising a comparison of the raw data with predetermined patterns and a generation of values of similarities of the raw data with the predetermined patterns; and wherein the second box is configured to select a movement category representative of the raw data from the similarity values of the first case and those of the second case.

3. The system according to claim 1, wherein the boxes are configured so that the raw data generated by the inertial platform of the first box is transferred to the second box where it is processed by the data processing module of the second box.

4. The system according to claim 1, wherein the data processing modules contained in the first and second boxes are configured to compare raw data generated by the inertial platform of the respective box with predetermined patterns and to generate similarity values of the raw data with the predetermined patterns, said predetermined patterns corresponding to a predetermined movement category, one of the processing modules being further configured to select a movement category representative of the raw data generated over a period of time from the similarity values of the first box and those of the second box.

5. The system according to claim 1, wherein the inertial platform includes at least one accelerometer and at least one gyroscope, and to which can be added further sensors.

6. The system according to claim 1, wherein each of the boxes is connected to an electronic board and one or more of the following: a GPS, physiological sensors, pressure sensors, temperature sensors or any air-conditioning system placed in the sole.

7. The system according to claim 1, wherein each of the boxes is configured to communicate with the other box and/or directly with the external terminal.

8. The system according to claim 1, wherein each electronic box includes at least one support pad.

9. The system according to claim 1, wherein each electronic box weighs less than 20 grams.

10. The system according to claim 1, wherein each electronic box has a thickness less than or equal to 7 mm.

11. The system according to claim 1, wherein each electronic box has a surface area on its largest side less than or equal to 10 cm$^2$.

12. The system according to claim 1, wherein each electronic box includes an outer casing, said outer casing being essentially made of a thermoplastic material enabling it to withstand high mechanical stresses, corresponding to at least 100,000 impacts of 1000 N at a frequency of 1 Hz or 100,000 impacts of 3000 N at a frequency of 2.6 Hz, said boxes being furthermore resistant to dust and humidity at a level of at least IP56.

13. The system according to claim 1, for associating one or more Android, IOS or other applications with secure data sharing with the user via the external terminal.

14. The system according to claim 1, wherein the power source of the electronic box can be a rechargeable battery, which can be recharged using different technologies:
   by a charger, with a connector flush with the sole;
   with a mechanical recharging device integrated into the sole, such as a piezoelectric device capable of supplying electrical energy from walking;
   with a non-contact device, for example by induction; or
   with a photovoltaic device.

15. A method of quantifying a user's posture and gait implemented within a system including a first box being integrated into a first sole and a second box being integrated into a second sole of a same pair of soles, each box comprising: an inertial platform, a data processing module, a data storage module configured to store information generated by the processing module, a means of communication and a power source, said method comprising:
   A step of generating raw data, by inertial platforms contained in the first and second boxes, said raw data being generated for a period of time and being a function of a user's gait,
   A step of pre-processing the raw data, by the data processing modules contained in the first and second boxes, comprising comparing the raw data with predetermined patterns and generating similarity values of the raw data with the predetermined patterns, said predetermined patterns corresponding to a predetermined category of movement, A step of communicating between the first and second box, comprising transmitting, by a communication module, similarity values from the second box to the first box, and A step of selecting, by the first box, a movement category representative of the raw data generated over the period of time, from the similarity values of the first box and those of the second box.

16. The method of quantifying a user's posture and gait according to the claim 15, further comprising a step of incrementing a counter associated with the selected category of movement and storing a new value of said counter.

17. The method of quantifying a user's posture and gait according to claim 15, wherein the pre-processing step includes a sub-step of calculating preliminary values of gait parameters by the first and second boxes.

18. The method of quantifying a user's posture and gait according to claim 17, further comprising a step of processing the preliminary values of gait parameters of the second box and of the first box so as to select preliminary values of gait parameters to be retained.

19. The method of quantifying a user's posture and gait according to claim 15, further comprising a prior learning step comprising defining a plurality of predetermined patterns of a user's gait.

20. The system according to claim 5, the further sensors comprising a magnetometer, a barometer, and/or an altimeter.

21. The system according to claim 7, wherein each of the boxes is configured to communicate with the other box and/or directly with the external terminal through short wave or high frequency signals of the Bluetooth or ANT+ type.

22. The system according to claim 8, wherein each electronic box includes at least two support pads.

* * * * *